United States Patent

Maruyama et al.

[11] Patent Number: 5,750,148
[45] Date of Patent: May 12, 1998

[54] METHOD FOR PREPARING SOLID ENTERIC PHARMACEUTICAL PREPARATION

[75] Inventors: Naosuke Maruyama; Hiroyasu Kokubo; Shin-Ichiro Nakamura, all of Niigata, Japan

[73] Assignee: Shin-Etsu Chemical Co., Ltd., Japan

[21] Appl. No.: 515,119

[22] Filed: Aug. 15, 1995

[30] Foreign Application Priority Data

Aug. 19, 1994 [JP] Japan .................. 6-195469
Dec. 1, 1994 [JP] Japan .................. 6-298094

[51] Int. Cl.$^6$ .................. A61K 9/36; A61K 9/62
[52] U.S. Cl. .................. 424/494; 424/461; 424/463; 424/480; 427/2.14; 427/2.21; 514/952; 514/781
[58] Field of Search .................. 424/461, 479, 424/480, 493, 494, 463; 427/2.14, 2.21; 514/781

[56] References Cited

U.S. PATENT DOCUMENTS 4,330,338  5/1982  Banker .................. 106/197

FOREIGN PATENT DOCUMENTS 0 541 369 A1  5/1993  European Pat. Off. .

OTHER PUBLICATIONS

Chemical & Pharmaceutical Bulletin, vol. 41, No. 2, Feb. 1993, Tokyo JP pp. 329–334, XP000354418, Shinji Narisawa et al., "Porosity–Controlled Ethylcellulose Film Coating. I. Formation of Porous Ethylcellulose Film in the Casting process and Factors Affecting Film–Density".

Patent Abstracts of Japan, C–269, Mar. 6, 1985, vol. 9, No. 52.

*Primary Examiner*—James M. Spear
*Attorney, Agent, or Firm*—Parkhurst & Wendel, L.L.P

[57] ABSTRACT

A cellulosic enteric base is dissolved in an organic solvent capable of being admixed with water in any rate or a mixed solvent of the organic solvent and water to give a polymer solution, followed by mixing the polymer solution with water, then removing the organic solvent to give a concentrate; adding an anionic surfactant to the concentrate and then drying to give polymer powder. The polymer powder is introduced into water to give an emulsion containing polymer particles having an average particle size of not more than 1 μm and the emulsion is dispersed in water containing a plasticizer to give a coating liquid. A drug is coated with the coating liquid to give a solid enteric pharmaceutical preparation.

6 Claims, No Drawings

5,750,148

METHOD FOR PREPARING SOLID ENTERIC PHARMACEUTICAL PREPARATION

BACKGROUND OF THE INVENTION

The present invention relates to a method for preparing a solid enteric pharmaceutical preparation provided with an enteric coating.

The solid enteric pharmaceutical preparation is provided with an enteric coating film for the purposes of protecting drugs having low resistance to acids from the attack of the acid in the stomach and of protecting the gastric mucous membrane from the attack of drugs which may stimulate and damage the wall of the stomach, and is dissolved after the arrival at the intestines in which the pharmaceutical preparation shows its pharmacological action. Cellulosic polymers have been used as examples of such coating bases among others. Specific examples of cellulosic polymers include cellulose acetate phthalate, hydroxypropylmethyl cellulose phthalate, hydroxypropylmethyl cellulose acetate succinate and carboxymethylethyl cellulose. These polymers are used in the coating treatment of drugs in the form of a solution in an organic solvent or an aqueous latex or an aqueous dispersion. However, the use of organic solvents has recently been regulated due to the problems of environmental pollution and correspondingly, coating treatments which make use of an aqueous system have widely been adopted.

There have already been proposed a variety of coating techniques which make use of aqueous systems. As methods for dispersing a cellulosic polymer in water, there have been known a method in which salts are added together with the polymer or the carboxyl groups present on the polymer are neutralized; and a method in which the polymer is pulverized into fine particles and then dispersed in water.

With regard to the former method, Japanese Patent Application Publication No. 61-56221 discloses a method which comprises the steps of emulsifying cellulose acetate phthalate, then adding a phosphoric acid salt as an antiflocculating agent and spray-drying the resulting emulsion to thus give polymer powder redispersible in water. In this case, the emulsification of the cellulose acetate phthalate is carried out according to the method disclosed in U.S. Pat. No. 4,177,177. In addition, Japanese Patent Provisional Publication No. 56-30913 discloses a method which comprises the step of dissolving cellulose acetate phthalate or hydroxypropylmethyl cellulose phthalate in water through neutralization thereof with ammonia to give an aqueous solution for use in the coating operation. Moreover, Japanese Patent Provisional Publication No. 58-135807 discloses a method which comprises the steps of neutralizing cellulose acetate phthalate or hydroxypropylmethyl cellulose phthalate with an alkali to dissolve it in water and then adding a carboxylic acid to the resulting solution. However, these methods suffer from a problem in that alkali or ammonium salts of carboxylic acids remain in the coating films of the resulting solid enteric pharmaceutical preparations. Accordingly, the resulting enteric pharmaceutical preparation is highly hygroscopic and does not have any reliable or stable quality.

With regard to the latter method, Japanese Patent Application Publication No. 56-12614 discloses a method which comprises the step of dispersing a cellulosic polymer having an average particle size of not more than 100 μm in water containing a gelling agent (a plasticizer) and accordingly having a boiling point of not less than 100° C. In addition, Japanese Patent Application Publication Nos. 57-53329 and 58-55125 teach the use of triacetin or triethyl citrate as such a gelling agent. In these methods, however, the polymers must be mechanically pulverized to prepare the aqueous dispersions for use in coating drugs and therefore, the particle size of the polymers present in the dispersions is not less than 1 μm. If the particle size is not less than 1 μm, a plasticizer must be used in a large amount and this in turn leads to softening of the polymer due to an increase of the temperature and hence cohesion and precipitation of the polymer. Moreover, the coating base exhibits poor film-forming ability due to a large particle size of the cellulosic polymer.

Moreover, Japanese Patent Application Publication No. 3-39490 discloses a method for eliminating drawbacks of the aqueous cellulose-coating techniques which comprises the step of reducing the particle size of the cellulosic polymer in the aqueous system through emulsification. In this method, the emulsification is performed according to the method disclosed in U.S. Pat. No. 4,177,177. More specifically, the method comprises the steps of dissolving a cellulosic polymer in an organic solvent incompatible with water to give an organic polymer solution; then adding a hydrocarbon having not less than 8 carbon atoms (such as cetyl alcohol) as a stabilizer and a surfactant to the polymer solution; and treating the polymer solution in a particular emulsifier such as a high pressure homogenizer to give an emulsion. In this method, however, the use of a particular emulsifier is required and the solvent used cannot completely be removed. As has been described above, the conventional aqueous coating liquids comprise additives such as stabilizers and surfactants in addition to the cellulosic polymer and these additives may often impair the resistance to acids and stability of the resulting enteric pharmaceutical preparation.

SUMMARY OF THE INVENTION

The present invention has been developed to eliminate the foregoing drawbacks associated with the conventional techniques and accordingly, it is an object of the present invention to provide a method for preparing a solid enteric pharmaceutical preparation which is coated with a coating liquid comprising a dispersed polymer particles having an average particle size of not more than 1 μm and which exhibits excellent resistance to acids.

According to the present invention, the foregoing object can effectively be accomplished by providing a method for preparing a solid enteric pharmaceutical preparation which comprises the steps of dissolving a cellulosic polymer in an organic solvent capable of being admixed with water in any proportion or a mixed solvent of the organic solvent and water to give a polymer solution; mixing the polymer solution with water and then removing the organic solvent to give a concentrate; adding an anionic surfactant to the concentrate and then drying to give polymer powder; introducing the polymer powder into water to give an emulsion containing polymer particles having an average particle size of not more than 1 μm; dispersing the emulsion in water containing a plasticizer to give a coating liquid; then coating a drug with the coating liquid to give a solid enteric pharmaceutical preparation.

DETAILED EXPLANATION OF THE INVENTION

Cellulosic polymers may serve as coating bases for preparing solid enteric pharmaceutical preparations. Examples of such cellulosic polymers include those used in the conventional organic solvent systems for coating drugs such as hydroxypropylmethyl cellulose phthalate, hydroxypropylmethyl cellulose acetate succinate, cellulose acetate phthalate, cellulose acetate trimellitate and carboxymethylethyl cellulose. These cellulosic polymers may be used alone or in any combination.

The organic solvent used in the present invention may be those capable of being admixed with water in any proportion. Examples thereof include alcohols such as methanol, ethanol and isopropanol; and ketones such as acetone and methyl ethyl ketone, which may be used in an amount sufficient for completely dissolving the cellulosic polymer. Alternatively, these organic solvents may be used in combination with water. The rate of water in such a mixed solvent may vary depending on the kinds of the cellulosic polymers to be dissolved therein, but is preferably not more than 60% by weight. This is because if it is more than 60% by weight, the resulting mixed solvent has a low content of the organic solvent and accordingly, the polymer solution does not undergo desired self-emulsification when it is poured into water.

The polymer solution preferably has a concentration of not more than 10% by weight and more preferably 2 to 10% by weight. If the concentration is not less than 10% by weight, the viscosity of the resulting solution is too high to give an emulsion containing fine polymer particles having a particle size of not more than 1 µm. Moreover, if it is not more than 2% by weight, the concentration of the aqueous emulsion ultimately obtained is too low to ensure a desired productivity.

The amount of water to be admixed with the polymer solution is preferably not less than 80% by weight and more preferably 80 to 150% by weight on the basis of the weight of the polymer solution. This is because if the amount of water is less than 80% by weight, the solvent is insufficiently dispersed in water and correspondingly the polymer is incompletely dispersed therein, while if it is not less than 150% by weight, the emulsion ultimately obtained has an extremely low concentration and should thus be subsequently concentrated.

Examples of surfactants usable herein are sodium lauryl sulfate and sodium dioctyl sulfosuccinate, with sodium lauryl sulfate being particularly preferred. The amount thereof to be added preferably ranges from 2 to 17 (weight ratio) and more preferably 5 to 12 (weight ratio) with respect to 83 to 98 (weight ratio) of the real quantity of the cellulosic polymer used. If an anionic surfactant is added in an amount falling within the range defined above, the dispersibility of the resulting emulsion is improved and accordingly, the film-forming ability thereof, i.e., the coating ability thereof is also improved. Moreover, the addition of an anionic surfactant results in the improvement of the stability to temperature of the resulting aqueous coating liquid.

If the added amount of the surfactant is less than 2 (weight ratio), the resulting polymer powder exhibits poor redispersibility in water, while if it is more than 17 (weight ratio), the resulting coating film shows a high water permeability and thus the resistance to acids thereof is impaired since the surfactant is water soluble by nature.

The coating liquid is specifically prepared according to the following procedures. A cellulosic polymer is dissolved in an organic solvent or a mixed solvent to give a polymer solution and then the polymer solution is mixed with water in a predetermined rate, while continuously and gently stirring them during the step using a stirring machine commonly used. The mixing operation is not significantly affected by the strength of the stirring operation. In this respect, care is necessary if the polymer solution is mixed with an aqueous phase. More specifically, if the aqueous phase is added thereto at a low rate, the polymer solution is not sufficiently dispersed in the aqueous phase because of a low concentration thereof and it is thus difficult to obtain an emulsion comprising polymer particles having an average particle size of not more than 1 µm. Subsequently, the organic solvent is removed from the emulsion through distillation or distillation under reduced pressure to give a concentrate. Alternatively, the removal of the organic solvent may be carried out by ultrafiltration.

After addition of an anionic surfactant, the concentrate thus obtained is formed into powder ready for use in preparing a coating liquid for coating drugs to give solid enteric pharmaceutical preparation. The formation of such powder is carried out using, for instance, a spray-dryer, a jet-dryer or a medium-fluidized dryer.

The powder is again dispersed in water to give an emulsion comprising polymer particles having an average particle size of not more than 1 µm and then the emulsion is dispersed in water containing a plasticizer to form a coating liquid.

The polymer concentration in the coating liquid preferably ranges from 3 to 20% by weight, in particular, 7 to 15% by weight. If the polymer concentration is not less than 20% by weight, the polymer particles may cause cohesion, while it is not more than 3% by weight, the amount of the coating liquid required for coating procedures substantially increases and the coating treatment of drugs requires a long period of time.

Examples of plasticizers usable herein are triethyl citrate, triacetin, dibutyl phthalate and diethyl phthalate, which may be used alone or in any combination. Among these, preferably used is triethyl citrate. The amount of the plasticizer to be used ranges from 5 to 100% by weight, in particular, 10 to 50% by weight on the basis of the weight of the polymer used. If the amount thereof is not more than 5% by weight, the resulting coating liquid cannot provide any complete and continuous coating film, while if it is not less than 100% by weight, polymer particles present in the coating liquid undergo cohesion.

The coating liquid may comprise other additives such as coloring agents, pigments, surface lubricants, thickening agents and/or auxiliary agents for film formation.

Examples of drugs to be coated with the coating liquid are enzyme-containing pharmaceutical preparations such as pancreatin, antipyretic analgesics such as sodium salt of diclofenac, cardiac glycosides such as digitoxin and electrolyte-containing pharmaceutical preparations such as potassium.

The coating treatment is carried out by spraying a solid enteric pharmaceutical preparation with the coating liquid using a coating device and then drying the liquid to form a film. The coating liquid may comprise pharmaceutically acceptable drugs and/or additives such as plasticizers, coloring agents, pigments and/or surface lubricants. Examples of plasticizers are triethyl citrate and triacetin. These drugs and/or additives may be used alone or in any combination. Examples of coating devices include a fluidized bed coater, a pan coater and a through-flow type rotary drum coater. A solid enteric pharmaceutical preparation is sprayed with the coating liquid using one of these devices and then the moisture is evaporated by blowing warmed air on the coated pharmaceutical preparation to thus form a film covering the solid enteric pharmaceutical preparation.

The present invention permits the preparation of a coating liquid which comprises dispersed polymer particles having an average particle size of not more than 1 μm and which is excellent in stability and film-forming ability and permits the preparation of a solid enteric pharmaceutical preparation excellent in resistance to acids through coating a drug with the coating liquid.

The present invention will hereinafter be described in more detail with reference to the following Examples, but the present invention is not limited to these specific Examples.

EXAMPLE 1

Hydroxypropylmethyl cellulose phthalate (HP-55, available from Shin-Etsu Chemical Co., Ltd.; 0.3 kg) was dissolved in 9.7 kg of an 8/2 (weight ratio) ethanol/water mixed solvent to give a polymer solution. Water (10 kg) was added to the polymer solution while stirring at a number of revolution of 100 rpm to emulsify the polymer. The resulting emulsion was distilled under reduced pressure using an evaporator to thus remove the solvent and then concentrated to a solid content of 10% by weight using a membrane for ultrafiltration.

Sodium lauryl sulfate (30 g; 10% by weight based on the weight of the HP-55) was added to the concentrate and then formed into powder in a spray-dryer. The resulting powder was found to have an average particle size of 10 μm and was excellent in flowability. The powder was again introduced into water to give a dispersion. As a result, the polymer particles present in the dispersion have an average particle size of 0.5 μm.

To 2595 g of water maintained at 25° C., there was added 105 g of triethyl citrate and 330 g of the foregoing powder was redispersed in the resulting solution to give a coating liquid.

Cylindrical granules of pancreatin having a diameter of 0.8 mm were sprayed with the coating liquid. A coating device, FLOWCOATER FLO-1 available from Freund Company was used for the spraying treatment. The spraying speed was set at 60 g/min during the treatment. After the spraying treatment, the moisture on the surface of the cylindrical granules of pancreatin was evaporated by blowing air having a temperature of 80° C., at a flow rate of 2.7 m³/min, on the cylindrical granules having a temperature of 33° C., while the waste gas temperature was set at 35° C. According to the foregoing procedures, there were prepared 6 kinds of cylindrical granules of pancreatin whose amounts of the coated films were 10, 12, 14, 16, 18 and 20% by weight respectively and these products were used as samples for disintegration test.

Then the amount of pancreatin dissolved and released into the gastric juice as a result of disintegration of the enteric coating film on the pancreatin granules thus prepared was determined using a dissolution tester according to the enteric test defined in Japanese Pharmacopoeia-12 as Disintegration Test. More specifically, the coated pancreatin granules were immersed in a first solution (artificial gastric juice) having a pH of 1.2 for 2 hours while maintaining the first solution at 37° C. (body temperature) to thus determine the amount of pancreatin released from the granules through the coating film. The results thus obtained are summarized in the following Table 1.

COMPARATIVE EXAMPLE 1

Triethyl citrate (105 g) was dissolved in 2595 g of water maintained at 15° C. and hydroxypropylmethyl cellulose phthalate (HP-55UF available from Shin-Etsu Chemical Co., Ltd.) having an average particle size of 5 μm was dispersed in the resulting solution to give a coating liquid.

Pancreatin granules were coated with the coating liquid according to the same method used in Example 1 and then the coated granules were subjected to the disintegration test defined in Japanese Pharmacopoeia—12 to determine the amount of pancreatin released from the granules through the coating film. The results thus obtained are summarized in the following Table 1.

TABLE 1

| Amount of Coating Film | Rate of Released Pancreatin After 2 hours (% by weight) | |
|---|---|---|
| (% by weight) | Example 1 | Comparative Example 1 |
| 10 | 17.8 | 48.3 |
| 12 | 3.3 | 42.9 |
| 14 | 1.0 | 23.6 |
| 16 | 0.7 | 6.8 |
| 18 | 0.5 | 1.4 |
| 20 | 0.3 | 0.2 |

As seen from Table 1, the rate of released pancreatin observed in Example 1 is lower than that observed in Comparative Example 1. This is because the coating liquid of Comparative Example 1 is inferior to the liquid of Example 1 in the film-forming ability since a cellulosic polymer having an average particle size of not less than 1 μm is dispersed in water containing a plasticizer in the Comparative Example 1.

EXAMPLE 2

Triethyl citrate (35 g) was dissolved in 865 g of water having a temperature of 25° C. and 110 g of powdery hydroxypropylmethyl cellulose phthalate (HP-55) prepared by the same method used in Example 1 was dispersed in the resulting solution to give a coating solution.

Lactose/corn starch type placebo tablets were sprayed with the resulting coating liquid. The spraying treatment was carried out using a small-sized through-flow type coater. The spraying speed was set at 10 g/min during the treatment. After the spraying treatment, the moisture on the surface of the tablets was evaporated by blowing air having a temperature of 70° C., at a flow rate of 2.7 m³/min, on the tablets having a temperature of 39° C., while the waste gas temperature was set at 36° C. According to the foregoing procedures, there were prepared 6 kinds of tablets whose amounts of the coated films were 5, 6, 7, 8, 9 and 10% by weight respectively and these products were used as samples for disintegration test. The coated tablets (100 tablets for each sample) were subjected to the disintegration test defined in Japanese Pharmacopoeia-12 to evaluate the number of abnormal tablets and the permeability of the first solution (artificial gastric juice) into the tablets. The results thus obtained are summarized in the following Table 2.

COMPARATIVE EXAMPLE 2

Triethyl citrate (35 g) was dissolved in 865 g of water maintained at 15° C. and hydroxypropylmethyl cellulose phthalate (HP-55F available from Shin-Etsu Chemical Co., Ltd.) having an average particle size of 8 μm was dispersed in the resulting solution to give a coating liquid.

Lactose/corn starch type placebo tablets were coated with the coating liquid according to the same method used in Example 1 and then the coated tablets were subjected to the disintegration test defined in Japanese Pharmacopoeia-12 to evaluate the number of abnormal tablets and the permeability of the first solution (artificial gastric juice) into the tablets. The results thus obtained are summarized in the following Table 2.

COMPARATIVE EXAMPLE 3

Triethyl citrate (35 g) was dissolved in 865 g of water maintained at 15° C. and hydroxypropylmethyl cellulose phthalate (HP-55UF available from Shin-Etsu Chemical Co., Ltd.) having an average particle size of 5 μm was dispersed in the resulting solution to give a coating liquid.

Lactose/corn starch type placebo tablets were coated with the coating liquid according to the same method used in Example 1 and then the coated tablets were subjected to the disintegration test defined in Japanese Pharmacopoeia-12 to evaluate the number of abnormal tablets and the permeability of the first solution (artificial gastric juice) into the tablets. The results thus obtained are summarized in the following Table 2.

TABLE 2

| Amt. of Film (wt %) | Rate of Abnormal Tablet (%) | | | Permeability of 1st Solution (%) | | |
|---|---|---|---|---|---|---|
| | Ex. 2 | Comp. Ex. 2 | Comp. Ex. 3 | Ex. 2 | Comp. Ex. 2 | Comp. Ex. 3 |
| 5 | 4.0 | 100.0 | 53.1 | 4.1 | — | — |
| 6 | 0 | 89.0 | 15.0 | 3.8 | — | 4.8 |
| 7 | 0 | 45.0 | 1.0 | 3.2 | 4.2 | 4.2 |
| 8 | 0 | 10.0 | 0 | 3.1 | 3.4 | 2.4 |
| 9 | 0 | 1.0 | 0 | 2.8 | 2.1 | 2.3 |
| 10 | 0 | 0 | 0 | 2.2 | 2.0 | 1.8 |

As seen from Table 2, the rates of abnormal tablet observed in Comparative Examples 2 and 3 are higher than that observed in Example 2. This is because the coating liquids of Comparative Examples 2 and 3 are inferior to the liquid of Example 2 in the film-forming ability since, in each Comparative Example, a cellulosic polymer having an average particle size of not less than 1 μm is dispersed in water containing a plasticizer in the Comparative Example 1.

What is claimed is:

1. A method for preparing a solid enteric pharmaceutical preparation comprising the steps of dissolving a cellulosic enteric base in an organic solvent capable of being admixed with water in any proportion or a mixed solvent of the organic solvent and water to give a polymer solution; mixing the polymer solution with water, then removing the organic solvent to give a concentrate; adding an anionic surfactant to the concentrate in an amount ranging from 2 to 17 weight ratio with respect to the real quantity of the cellulosic enteric base ranging from 83 to 98 weight ratio, then drying the mixture to give polymer powder; introducing the polymer powder into water to give an emulsion containing polymer particles having an average particle size of not more than 1 μm; dispersing the emulsion in water containing a plasticizer to give a coating liquid; and then coating a drug with the coating liquid.

2. The method for preparing a solid enteric pharmaceutical preparation as set forth in claim 1 wherein the cellulosic enteric base is at least one member selected from the group consisting of hydroxypropylmethyl cellulose phthalate, hydroxypropylmethyl cellulose acetate succinate, cellulose acetate phthalate, cellulose acetate trimellitate and carboxymethylethyl cellulose.

3. The method for preparing a solid enteric pharmaceutical preparation as set forth in claim 1 wherein the organic solvent is at least one member selected from the group consisting of methanol, ethanol, isopropanol, acetone and methyl ethyl ketone; the rate of water in the mixed solvent is not more than 60% by weight; the polymer concentration of the polymer solution is not more than 10% by weight; and the amount of water in which the polymer solution is dispersed is not less than 80% by weight on the basis of the amount of the polymer solution.

4. The method for preparing a solid enteric pharmaceutical preparation as set forth in claim 1 wherein the anionic surfactant is sodium lauryl sulfate and/or sodium dioctylsulfosuccinate.

5. The method for preparing a solid enteric pharmaceutical preparation as set forth in claim 1 wherein the plasticizer is at least one member selected from the group consisting of triethyl citrate, triacetin, dibutyl phthalate and diethyl phthalate; the amount of the plasticizer to be used ranges from 5 to 100% by weight on the basis of the amount of the cellulosic polymer.

6. The method for preparing a solid enteric pharmaceutical preparation as set forth in claim 1 wherein the polymer concentration of the coating quid ranges from 3 to 20% by weight.

* * * * *